United States Patent
Marchese et al.

(10) Patent No.: US 8,067,037 B2
(45) Date of Patent: Nov. 29, 2011

(54) TREHALOSE-CONTAINING TOPICAL DRYING COMPOSITION AND METHOD OF USING SAME

(76) Inventors: Frank P. Marchese, Bronxville, NY (US); Xinghua Pan, Hamden, CT (US); Harold J. Mermelstein, Bronx, NY (US)

( * ) Notice: Subject to any disclaimer, the term of this patent is extended or adjusted under 35 U.S.C. 154(b) by 303 days.

(21) Appl. No.: 12/214,863

(22) Filed: Jun. 24, 2008

(65) Prior Publication Data

US 2009/0317493 A1  Dec. 24, 2009

(51) Int. Cl.
*A01N 60/00* (2006.01)
*A01N 43/04* (2006.01)
*A61K 30/00* (2006.01)
*A61K 31/715* (2006.01)

(52) U.S. Cl. .......................................... 424/725; 514/53
(58) Field of Classification Search .................. 424/725; 514/53

See application file for complete search history.

(56) References Cited

U.S. PATENT DOCUMENTS

| | | | |
|---|---|---|---|
| 5,160,732 A | 11/1992 | Katsoulis et al. | |
| 5,179,220 A | 1/1993 | Katsoulis et al. | |
| 5,653,970 A * | 8/1997 | Vermeer | 424/70.24 |
| 5,705,171 A | 1/1998 | Iovanni et al. | |
| 5,911,975 A | 6/1999 | Mendolia et al. | |
| 6,231,837 B1 * | 5/2001 | Stroud et al. | 424/59 |
| 2001/0031249 A1 | 10/2001 | Oku et al. | |
| 2007/0003502 A1 | 1/2007 | Tanabe et al. | |
| 2007/0020220 A1 | 1/2007 | Osborne et al. | |
| 2009/0220444 A1 | 9/2009 | Teckenbrock et al. | |

* cited by examiner

*Primary Examiner* — Sreeni Padmanabhan
*Assistant Examiner* — Kendra D Carter

(57) ABSTRACT

A topical drying composition is providing containing trehalose as the effective moisture (sweat) removing ingredient. The composition may be used in aqueous form or preferably as a cream and in addition to trehalose it contains several ingredients such as sorbitan monolaurate, polysorbitan, a moisturizer, a thickener, a softener, an antibacterial agent and a pH adjusting component to adjust the pH of the composition between about 5.5 to about 7.5. Sterilized water is used as the carrier for the composition.
The topical composition can be applied to the area which is vulnerable to sweating after vigorous exercise in order to moisturize sweating on the skin.

7 Claims, No Drawings

TREHALOSE-CONTAINING TOPICAL DRYING COMPOSITION AND METHOD OF USING SAME

FIELD OF THE INVENTION

The present invention relates generally to topical drying composition and is particularly related to topical drying composition containing effective amount of trehalose as the drying ingredient. In its more specific aspect, this invention relates to a topical drying composition containing an effective amount of trehalose which enhances drying the skin when it is topically applied to the skin of persons, such as athletes, after perspiration due to exercise, such as playing tennis, golf, aerobics or after other strenuous sweat-producing activities.

BACKGROUND OF THE INVENTION

Trehalose is a known non-reducing disaccharide composed of $D_+$glucose units. It is a white, odorless, sweet-tasting powder and, like maltose, is about 45% as sweet as sugar and has a very low hydroscopicity (moisture attraction). Trehalose is found in honey, bread, beer and seafood and there are several prior art patents relating to various uses of trehalose. For example, U.S. Pat. No. 4,839,164 discloses cosmetic compositions containing trehalose which increase the penetration of certain therapeutically beneficial ingredients into the skin thereby enhancing the therapeutic effects of those ingredients on the skin. The trehalose is used in a pharmaceutically acceptable carrier and several trehalose-containing formulations are disclosed in said patent, such as shampoo formulations, hair-conditioning formulations, skin care gel formulations, lotions, and skin care creams.

U.S. Pat. No. 5,543,513 discloses the use of anhydrous trehalose as a desiccant for dehydrating various products such as dehydrated food as well as dehydrated pharmaceuticals. High-quality food products having reduced moisture content can be prepared by incorporating anhydrous trehalose into food products having relatively high moisture content thereby converting the anhydrous trehalose into hydrous crystalline trehalose.

U.S. Pat. No. 6,555,526 discloses an ophthalmic pharmaceutical composition comprising trehalose as the effective ingredient. As disclosed in said patent, there are three types of optical isomers of trehalose, i.e., $\alpha,\alpha$-trehalose, $\alpha,\beta$-trehalose and $\beta,\beta$-trehalose. All isomers exert therapeutic and/or prophylactic effect on signs of Sjorgen syndrome.

U.S. Pat. No. 6,723,170 discloses a crystalline trehalose dihydrate with low hydroscopicity. Variety of uses are disclosed for the crystalline trehalose dihydrate, including its use as a sweetener, taste-improving agent, in feeds and pet foods for animals, in soaps, skin creams, body shampoos, hair creams, moisture-controlling agent and a host of other uses disclosed in said patent.

Notwithstanding a variety of uses of trehalose disclosed in the prior art patents, none, so far is known, recognize the efficacy of trehalose for use in a topical drying composition.

Therefore, it is an object of the present invention to use trehalose in a topical drying composition.

It is a further object of the present invention to provide a topical drying composition containing trehalose as the effective ingredient for sweat removal.

It is also an object of this invention to provide a topical drying composition containing effective amount of trehalose and a suitable carrier.

It is another object of this invention to provide a method of drying the skin by the topical application of trehalose-containing composition in which trehalose is the effective skin drying ingredient.

The foregoing and other objects and features of the present invention will be more clearly understood from the ensuing description and illustrative examples.

SUMMARY OF THE INVENTION

This invention provides a topical drying composition containing an effective amount of trehalose, in hydrous and/or anhydrous form, in an acceptable carrier such as sterilized water. The composition further includes sorbitan monolaurate, polysorbitan and a pH adjuster in an amount to adjust the pH of the composition between about 5.5 to about 7.5. The pH adjusting ingredient may be sodium chloride, potassium chloride, sodium hydrogen phosphate and borax, or a mixtures thereof.

The composition of this invention may be prepared in cream form and thus may include a thickener such as carbomer Ultrex 10, EDTA softener, moisturizer such as dimethicone 200, cocoa butter to impart smoothness to the cream, and antibacterial agent such as sodium benzoate and potassium benzoate.

The composition, whether in aqueous solution form or as a cream, is applied to the skin in the areas which are vulnerable to perspiration after vigorous exercise. When tested by several volunteers, they responded with virtually no perspiration after several hours of vigorous exercise in a gym on a bicycle or treadmill, or even after several miles of jogging when normally the subjects experienced perspiration in the past when they did not apply the composition.

DETAILED DESCRIPTION OF THE INVENTION

The topical drying compositions of this invention are provided as aqueous solutions or preferably as creams with desirable consistency. The trehalose ingredient in these compositions may be the hydrous form, anhydrous form or mixture of the hydrous and anhydrous trehalose, and the composition may include a "buffer" as hereinafter described in order to control the pH at a desired level. An antibacterial agent may also be included in or due to impart antibacterial property to the composition.

The following illustrative examples describe the preparation of various trehalose-containing compositions containing various other necessary and/or desired ingredients in addition to the essential ingredients. All parts are expressed by weight and weight percent.

EXAMPLE 1

204 grams of distilled water was charged to a reaction vessel equipped with a stirrer, at room temperature and ambient pressure. Thereafter, 2.5 grams of a thickener, (Ultrex 10), polyacrylic acid thickener available from B.F. Goodrich, Co. was added slowly and mixed with the water in the vessel, followed by addition of 1.5 grams of ethylene dramine tetra acetic acid (EDTA), with continuous agitation resulting in mixture A. The clear mixture was then heated to 45° C.

A separate mixture (Mixture B) was prepared containing 40 grams sorbitan monolaurate (Arlacel 20 available from Ruger Chemical Co., Inc.) 85 grams of polysorbate (Tween 20 available from Ruger Chemical Co., Inc.) 23 grams of cocoa butter, 10 grams of dimethicone 200 (polydimethylsiloxane) available from Dow Corning, a moisturizer having a viscosity of 700 cps, 3 grams of 1% of sodium benzoate and 1.5 grams of 1% potassium sorbate (antibacterial agent), and the resulting mixture was heated to 60° C. with constant stirring. Mixture B was then slowly added to the vessel containing mixture A resulting in the formation of homogeneous cream. The resulting cream was allowed to cool to 35° C., followed by the addition of aqueous solution of 40 grams of hydrous trehalose in 100 grams of sterilized water and mixed for 2 hours. The following table lists the ingredients of the resulting cream.

TABLE 1

| Ingredient | Parts by Wt. | Wt. % |
| --- | --- | --- |
| Sterilized water | 204.0 | 68.74 |
| Carbopol Ultrex 10[1] | 2.5 | 0.06 |
| EDTA tetrasodium | 1.5 | 0.04 |
| Sorbitan monolaurate | 40 | 10.3 |
| Cocoa butter | 23.0 | 5.1 |
| Polysorbitan (Tween 20) | 8.5 | 2.18 |
| Dimethicone 200 | 10.0 | 2.57 |
| Sodium benzoate 1% | 3.0 | 0.77 |
| Potassium sorbate 1% | 1.5 | 0.04 |
| Hydrous Trehalose | 40.0 | 10.2 |
| TOTAL | 334 | 100.0 |

[1]carboxy polymethylene
The pH of the resulting cream was adjusted to 6.5 with 5% solutions of sodium hydroxide.

Clinical Test on Formula No. 1

Six male volunteers ages 24, 35, 37, 42, 43 and 50 applied the cream preparation in Example 1 to the axilla of one arm only. After exercising in a gym on a bicycle and a treadmill for (4) hours, they all reported that the axilla to which the cream was applied was completely dry but the axilla of the other arm to which the cream was not applied was wet with moisture.

EXAMPLE 2

Following a similar procedure as in Example 1, another cream formulation was prepared having the ingredients listed in the following table

TABLE 2

| Ingredient | Parts by Wt. | Wt. % |
| --- | --- | --- |
| Sterilized water | 203.9 | 64.9 |
| Carbopol Ultrex 10 | 2.5 | 0.7 |
| EDTA | 1.5 | 0.5 |
| Sorbitan monolaurate (Arlacel 20) | 27.7 | 8.8 |
| Cocoa butter | 23.1 | 7.3 |
| Polysorbate 20 (Tween 20) | 8.3 | 2.6 |
| Dimethicone 200 | 10.0 | 3.2 |
| Hyamine | 0.1 | 0 |
| Hydrous Trehalose | 38.0 | 12 |
| TOTAL | 315.10 | 100 |

The pH of the resulting cream was adjusted to 6.4 with 10% sodium hydroxide solution Clinical Test on Formula No. 2

Three female volunteers ages 49, 53 and 59 applied the cream formulation obtained in Example 2 to both of their armpits. After exercising vigorously on a treadmill for 2 hours, they reported minimal wetness compared to their normal experience when they did not use the cream.

EXAMPLE 3

The formulations in the following table was made by the same general procedure heretofore described and was tested for its efficacy.

TABLE 3

| Ingredient | Parts by Wt. | Wt. % |
| --- | --- | --- |
| Sterilized water | 203.9 | 69.69 |
| Carbomer thickener (Ultra 10) | 2.5 | .85 |
| Tetra Sodium EDTA | 1.5 | .51 |
| Sorbitan monolaurate | 27.7 | 9.46 |
| Shea butter | 23.1 | 7.89 |
| Polysorbate 20 (Tween 20) | 8.3 | 2.83 |
| Dimethicone 200 | 10.0 | 3.41 |
| Hyamine | 0.7 | .24 |
| Hydrous Trehalose | 15.0 | 5.12 |
| TOTAL | 292.7 | 100 |

The pH of the resulting cream was adjusted to 6.4 with 5% sodium hydroxide solution Clinical Test on Formula No. 3

Six male volunteers ages 24, 35, 37, 42, 43 and 50 applied the cream to the axilla of one arm only. After exercising vigorously in a gym using a bicycle and treadmill for (4) hours they reported very little sweating in the armpit to which they applied the cream but the other arm sweated as normal.

The same 6 volunteers applied the cream formulation of Example 3 but without including trehalose. All reported significant sweating of the arm.

EXAMPLE 4

In this example the formulation did not contain the dimethicone moisturizer but contained larger amount of trehalose.

TABLE 4

| Ingredient | Parts by Wt. | Wt. % |
| --- | --- | --- |
| Sterilized water | 204.0 | 64.95 |
| Carbopol Ultrex 10 | 2.5 | 0.80 |
| Tetra Sodium EDTA | 1.5 | 0.50 |
| Sorbitan monolaurate | 28.0 | 8.90 |
| Cocoa butter | 23.0 | 7.30 |
| Polysorbate 20 (Tween 20) | 8.5 | 2.70 |
| Sodium Benzoate 1% | 3.0 | 0.95 |
| Potassium Sorbate 1% | 1.5 | 0.50 |
| Hydrous Trehalose | 42.0 | 13.40 |
| TOTAL | 314 | 100 |

The pH of the resulting cream was adjusted to 6.4 with 5% sodium hydroxide solution Clinical Test on Formula No. 4

Six male volunteers ages 21, 22, 27, 29, 30 and 34 applied the cream to the axilla of both arms. After exercising vigorously in a gym using a bicycle and a treadmill for 3.5 hours, all volunteers reported negligible wetness in their armpits.

EXAMPLE 5

Part A
300 grams of distilled water was combined with 2.5 grams of carbopol 934 and allowed to form a clear solution. Then 1.5 grams of EDTA was added and the mixture was stirred until it dissolved. This mixture was then heated to 55° degrees centigrade with stirring.

Part B

In a separate vessel 23 grams of cocoa butter was combined with 28 grams of sorbitan monolaurate, 8.5 grams polysorbate 20, and 10 grams of dimethicone. Then 0.4 grams of sodium chloride, 0.15 grams of potassium chloride, 0.15 of sodium hydrogen phosphate and 0.1 of borax were added, and the entire mixture was then heated to 60° degrees centigrade.

Part C

Part B was then added slowly to Part A with vigorous stirring forming Part C, a white cream.

Part D 68.5 grams of trehalose, 3 grams of 1% sodium benzoate and 1.5 potassium sorbate were added to Part C and the mixed well for several hours to form a cream having a pH of 7.0

Table 5 below lists the ingredients and the composition.

TABLE 5

| Ingredient | Parts by Wt. | Wt. % |
|---|---|---|
| Distilled water | 300.00 | 67.11 |
| Carbopol 934 | 2.5 | .56 |
| Tetrasodium EDTA | 1.5 | .33 |
| Cocoa Butter | 23.0 | 5.14 |
| Sorbitan monolaurate | 28.0 | 6.26 |
| Polysorbate 20 | 8.5 | 1.90 |
| Dimethicone 200 | 10.0 | 2.23 |
| Sodium Benzoate 1% | 3.0 | .67 |
| Potassium Sorbate 1% | 1.5 | .33 |
| Trehalose Anhydrous | 68.5 | 15.30 |
| Sodium Chloride | 0.4 | 0.09 |
| Potassium Chloride | 0.15 | .03 |
| Sodium hydrogen phosphate | 0.15 | 0.03 |
| Borax | 0.1 | .02 |
| TOTAL | 447.3 | 100.00 |

The pH of the resulting cream was adjusted to 6.4 with 5% sodium hydroxide solution Clinical Test on Formula No. 5

The test was conducted on two male volunteers ages 55 and 67. Each volunteer applied the cream to his face, forehead and one armpit and entered a sauna. After ½ hour they emerged from the sauna and were examined. Their face and neck showed signs of complete dryness and their armpits were completely dry. Their back and legs were damp with perspiration.

The test was also conducted on three basketball players ages 18, 21 and 23 on an outside court at 82° F. Each covered his hands and forehead (without band) and armpits with the cream. After playing for ½ hour, their hands and forehead were free of moisture. After 2.5 hours their hands and forehead was still free of moisture.

The test was also conducted on golfers ages 45, 56, 60 and 64 on a very warm day 90° F. Each covered both hands with the cream. After eight holes of play their hands were dray and they all claimed that the grip on the club improved with better control and they did not even need to wear a glove.

The method of use of the composition simply involves applying by hand a generous amount to the skin in the area vulnerable to sweating, and spreading the composition to cover that area. When using the composition in aqueous solution form, it may be applied similarly, or from a container with an applicator or a spray nozzle.

While the aforementioned compositions have been described with certain degree of specificity, it is obvious to those skilled in the art of formulating such compositions that several changes or modification may be made which are nevertheless suggested from the foregoing detailed description.

Optionally, other ingredients may be included in the cream formulation described in the foregoing examples. For example, the addition of a bovine collagen (1% aqueous solution of alphahydroxy proline help restore the elasticity in the skin along with 1% aqueous solution of elastin. Also, while the hydrous trehalose is used as the effective ingredient, anhydrous trehalose may be used instead, or in combination with hydrous trehalose. Also aqueous buffer solutions of trehalose, hydrous and/or anhydrous have been found effective topical drying compositions.

The invention claimed is:

1. A composition for use as topical drying composition consisting essentially of:
    (a) trehalose in an amount effective for removal of sweat or moisture from the skin,
    (b) from about 3% to about 30% weight percent sorbitan monolaurate,
    (c) from about 1% to about 10% weight percent polysorbitan,
    (d) an acceptable carrier for said composition, and
    (e) a pH adjusting ingredient in an amount sufficient to adjust the pH of the composition between 5.5 to 7.0.

2. A topical drying composition as in claim 1 wherein said acceptable carrier in sterilized water.

3. A composition for use as topical drying composition in the form of a cream wherein said composition consists essentially of:
    (a) trehalose in an amount effective for removal of sweat or moisture from the skin,
    (b) from about 6% to about 9% weight percent sorbitan monolaurate,
    (c) from about 2% to about 3% weight percent polysorbitan, and
    (d) from about 6.7% to about 7.5% weight percent cocoa butter,
    (e) an acceptable carrier for said composition,
    (f) a pH adjusting ingredient in an amount sufficient to adjust the pH of the composition between about 5.5 to about 7.5, (g) from about 1% to about 10% weight percent moisturizer, (h) from about 1% to about 10% weight percent thickening agent, and (i) an effective amount of antibacterial agent.

4. A topical drying composition as in claim 3 wherein said acceptable carrier is sterilized water.

5. A topical drying composition as in claim 3 wherein said moisturizer is polydimethylenesiloxane and said thickening agent is carboxy polymethylene.

6. A topical composition as in claim 1 wherein said pH adjusting ingredient is selected from the group consisting of sodium chloride, potassium chloride, sodium hydrogen phosphate and borax, or mixtures thereof.

7. A topical drying composition as in claim 3 wherein said pH adjusting ingredient is selected from the group consisting of sodium chloride, potassium chloride, sodium hydrogen phosphate and borax, or mixtures thereof.

* * * * *